United States Patent [19]
Lillo

[11] Patent Number: 4,603,109
[45] Date of Patent: Jul. 29, 1986

[54] METHOD AND APPARATUS FOR CONTACTING REACTANTS IN CHEMICAL AND BIOLOGICAL REACTIONS

[75] Inventor: Eric Lillo, Worcester, Mass.

[73] Assignee: Norton Company, Worcester, Mass.

[21] Appl. No.: 616,442

[22] Filed: Jun. 1, 1984

[51] Int. Cl.$^4$ .................. C12P 1/00; C12N 11/14; C12N 11/06
[52] U.S. Cl. .................. 435/41; 435/176; 435/181; 435/288; 422/192; 422/193; 422/197; 423/659; 423/DIG. 17
[58] Field of Search .............. 422/192, 197, 188, 190, 422/193, 194, 55, 56; 435/176, 181, 182, 183, 175, 288, 299, 310, 317, 41; 423/DIG. 13, DIG. 14, DIG. 17, 659; 210/615-619, 638

[56] References Cited

U.S. PATENT DOCUMENTS

| | | | |
|---|---|---|---|
| 3,353,982 | 11/1967 | Blaha | 117/8 |
| 3,359,622 | 12/1967 | Meyer et al. | 29/420.5 |
| 3,888,629 | 6/1975 | Bagshawe | 422/61 |
| 3,984,044 | 10/1976 | Breton et al. | 228/198 |
| 4,090,022 | 5/1978 | Tsao et al. | 435/179 |
| 4,153,510 | 5/1979 | Messing et al. | 435/176 |
| 4,175,153 | 11/1979 | Dobo et al. | 428/398 |
| 4,205,971 | 6/1980 | Abthoff et al. | 55/337 |
| 4,239,854 | 12/1980 | Hirohara et al. | 435/180 |
| 4,321,141 | 3/1982 | Messing | 435/176 |
| 4,350,765 | 9/1982 | Chibata et al. | 435/182 |
| 4,384,045 | 5/1983 | Ho et al. | 502/27 |
| 4,440,853 | 4/1984 | Michaels et al. | 435/84 |

FOREIGN PATENT DOCUMENTS

| | | |
|---|---|---|
| 1333105 | 6/1968 | France . |
| 2177881 | 11/1973 | France . |
| 2251351 | 6/1975 | France . |
| 8004205 | 2/1980 | France . |
| 8002787 | 2/1980 | France . |
| 8106340 | 3/1981 | France . |
| 604826 | 9/1978 | Switzerland . |
| 1286403 | 8/1972 | United Kingdom . |
| 1410551 | 10/1975 | United Kingdom . |
| 1468928 | 3/1977 | United Kingdom . |

OTHER PUBLICATIONS

Advertising material from Ceraver Ceramiques Industrielles, Paris, France.

Primary Examiner—David L. Lacey
Attorney, Agent, or Firm—Frank S. Chow

[57] ABSTRACT

The present invention is directed to novel methods and apparatus for conducting chemical and biological reactions. A reactor is provided that includes a reaction matrix member formed from microporous ceramic. A chemical or biological material is fixed within the pores of the porous matrix, and reaction solution is passed through the porous matrix member at a controlled rate. Preferably, the matrix member is tubular in shape and comprises a plurality of concentric layers of ceramic material, each layer having a substantially uniform pore size, but the plurality of layers having a progressively decreasing pore size with respect to the preceding layer. Each layer may also have a different thickness than other layers. Reaction solution is introduced into an axial bore through the ceramic matrix member, and the product solution is collected from the outside of the ceramic matrix member. Optionally, lumens within one or more adjacent ceramic layers, and/or spaces between layers can be provided.

9 Claims, 7 Drawing Figures

METHOD AND APPARATUS FOR CONTACTING REACTANTS IN CHEMICAL AND BIOLOGICAL REACTIONS

BACKGROUND

1. Field of the Invention

The present invention relates to methods and apparatus utilized in conducting continuous chemical and biological reactions. More particularly, the present invention is directed to construction and use of reactors (such as bioreactors) for use in connection with chemical and biological reactions.

2. The Prior Art

As a result of the dramatic increase in knowledge concerning biological reactions in recent years, and also because of vast improvements in techniques for isolating particular enzymatic compounds, there has developed a substantial industrial reliance upon biochemical reactions to obtain desired biochemical products.

Reactions involving biological materials are typically conducted in reaction vessels generally known as "bioreactors." The simplest type of bioreactor is nothing more than a vat into which is introduced the biological material, such as a microorganism or enzyme, together with appropriate reactants and/or nutrients. After an appropriate period of time, the products are separated from the biological material such as by use of a polymer membrane filter, and the biological material is returned to the bioreactor.

It will be appreciated that use of a vat as a bioreactor results in a batch process, thereby yielding an intermittent production of products. Also, because reaction products that form early in the batch cycle are retained in the vat during the entire batch cycle, it is not uncommon for desired products to degrade or to undergo additional undesirable reactions. Further, this batch type of bioreactor allows for very little control over reaction parameters other than gross parameters such as temperature.

Although a vat-type bioreactor is adequate for some biological reactions, because of the foregoing problems, many reactions are performed in more recently-developed bioreactors which comprise a column filled with glass beads. In such a "packed column" bioreactor, the glass beads are first treated so that the surface of the beads are coated with a thin film of an organic substance which will attract and adhere to the biological material to be reacted; various silanes and olefins are often used for this purpose. A solution containing the biological material is then fed through the column so that the biological material will become affixed to the organic coating on the glass beads and thus be held in the column. Finally, a solution containing reactants is introduced into the column, and products and unreacted reactants are collected at the bottom of the column.

One important advantage of the packed column-type bioreactor over a vat-type bioreactor is that the packed column-type is a semi-continuous system that provides a more relatively constant supply of reaction products than obtained in vat-type bioreactors. Another advantage of the packed column-type bioreactors is that the size of the glass beads and the solution flow rate can be adjusted in order to control the reaction occurring within the column. Further, since the reaction products are continually removed from the system, the likelihood of occurrence of degradation or unwanted reactions is significantly reduced as compared to the vat-type bioreactor.

However, while much better than a vat-type bioreactor, since the reaction rate is primarily diffusion limited, a packed column-type bioreactor still provides for little control of many reaction parameters, particularly at the reaction site. Also, since only the surfaces of the beads have biological material attached thereto, there is much unused space within the column; hence, it is typically necessary to use very large columns. In addition, although products and unused reactants are continually removed from the column system, thereby significantly reducing the amount of unwanted side reactions as compared to such reactions in a vat-type bioreactor, some product is generated near the entry point of the column, and must thus negotiate substantially the entire length of the column before being removed from the system. Thus, the potential for significant degradation and unwanted side reactions still remains. One further problem when utilizing columns is the difficulty in cleaning and sterilizing the column and beads between uses; it is a burdensome and time-consuming task to unpack, clean, and repack a column between uses.

Another recently developed reactor involves the use of thin microporous sheets of a polyvinylchloride-silica (PVC-silica) material that are placed within the reactor so that reaction solution flows through the microporous sheets. Various chemicals and enzymes are capable of binding to active sites (attributed to the presence of silica) within the porous matrix of these sheets.

However, the use of PVC-silica sheets in a bioreactor also suffers from significant disadvantages. For instance, the rate of diffusion of fluid across a microporous PVC-silica membrane is inversely proportional to the thickness of the membrane. Thus, in order to accommodate high volume throughput, it is extremely advantageous to provide a very thin membrane. However, rarely will acceptable volumes of fluid diffuse through even a very thin membrane without application of pressure as a driving force. Typically, it is necessary to apply substantial pressure in order to drive acceptable volumes of fluid through such membranes.

Unfortunately, the use of high pressures across a very thin PVC-silica membrane results in substantial stress on the membrane, typically resulting in degradation or deformation of the membrane. Deformation causes the pore sizes to become effectively larger in some places, thereby permitting oversized fluid components to pass therethrough, and undersized in other locations, thereby filtering out fluid components that should be permitted to pass through the membrane. Frequently, the thickness of the membrane must be substantially increased so that the membrane will be capable of withstanding the considerable stress imparted by the pressurized fluid. This, of course, is somewhat self-defeating since the act of thickening the membrane acts to reduce the volume throughput, thereby mandating even greater pressures. As a result, a less than optimum compromise must be made with respect to the pressures used to drive fluid through the membrane, and the thickness of the membrane.

Membranes formed from materials such as polysulfone and polypropylene have also been utilized as matrix material in bioreactors. In addition to problems similar to those discussed above, bioreactors utilizing membranes formed from these materials have exhibited problems referred to as "cell release" due to the deform-ability of the material under pressure that builds up due simply to cell growth.

Another porous membrane-type bioreactor that has been utilized is provided with a membrane constructed from ceramic rather than from a PVC-silica material. One advantage of using a ceramic membrane is that it is less subject to deformation than a PVC-silica membrane or a membrane constructed from a polysulfone or polypropylene material. However, a ceramic membrane remains subject to degradation under high pressures if the membrane is too thin; hence, it remains necessary to compromise between the pressures used to drive fluid through the membrane, and the thickness of the membrane.

A further difficulty encountered when using membrane sheets is that due to fluid dynamics, flow through the center of the sheet will be significantly faster than flow through the sheet near the edges. As a result, when the sheet is used as a support matrix for a chemical or biological material to be used in effecting a desired reaction, the flow of reaction solution past the chemical or biological material will be much greater in some portions of the membrane than in others. Since the flow rate is an important determinant of reaction rate and of the efficiency of the reaction, this difference in flow rate from location to location on the membrane can have a substantial adverse effect on the efficiency of the reaction system.

One further difficulty sometimes encountered when using microporous membranes is that the use of high pressures can sometimes be detrimental to various fluid components. For instance, high pressures can be extremely detrimental to some cellular components that might be used to effect biological reactions. Also, use of high pressures might cause chemical or biological materials fixed within the pores of material to break loose and be carried away in the reaction solution. Thus, in some cases, the use of a typical PVC-silica membrane or a ceramic membrane requires use of relatively low pressures, with a correspondingly low volume throughput. However, because of the flexibility of PVC-silica material, it is sometimes not feasible to provide PVC-silica membranes thin enough to permit adequate flow rates when using such low pressures, and yet capable of maintaining a controlled pore size.

In view of the foregoing, it will be appreciated that it would be a substantial advancement if an improved bioreactor could be provided that was capable of increased control over reaction parameters. It would also be a significant advancement if a new bioreactor were provided that had the capability to collect reaction products separately from reactants and unwanted by-products, and that could minimize unwanted side reactions. Additionally, it would be a significant advancement if a new bioreactor were to be provided that could be readily cleaned and sterilized for reuse. Such a bioreactor is described and claimed herein.

BRIEF SUMMARY AND OBJECTS OF THE INVENTION

The present invention is directed to novel methods and apparatus for conducting chemical and biological reactions. The apparatus of the invention comprises a bioreactor including a ceramic matrix member formed from a porous material. A chemical or biological material capable of effecting a desired reaction is caused to be fixed within the pores of the porous ceramic matrix member, and a reactant solution is passed therethrough at a controlled rate. Unused reactants and products are then recovered.

In one preferred embodiment, the ceramic matrix member is generally tubular in shape, is constructed so as to have a uniform porosity throughput, and is provided with a bore through which reaction solution is introduced into the ceramic matrix member under pressure. A portion of the reaction solution passes through the ceramic matrix member where it reacts with the chemical or biological material which is fixed within the pores of the ceramic matrix material. Unused reactants and reaction products are collected from the exterior of the matrix.

Other presently preferred embodiments involve the use of multiple layers of ceramic matrix materials having differing porosities, and perhaps different thicknesses, so as to selectively filter various solution components. In this preferred embodiment, each pervious ceramic microfilter is formed of a plurality of sintered layers of ceramic material, each layer having a different controlled pore size. The term "controlled pore size" is meant to refer generally to the effective average pore size of the ceramic material. It has been found advantageous to form layers of differing pore size in which the fine grains which make up the thinner filtering layer adhere onto the surface of the larger grains of the support layer, but they do not penetrate significantly into the grains of the support layer. Thus a structure is obtained such that the support and filtering layers are bonded to form a rigid ceramic having satisfactory structural integrity. The use of such multiple layers can be used to minimize degradation and unwanted side-reactions and can be used to accomplish at least partial separation of the various components of the reaction solution upon completion of the reaction.

The use of a very small pore size in forming the ceramic matrix member provides extremely large surface areas for fixing the reactant chemical or biological material. Accordingly, it is possible to utilize relatively narrow-diameter, tubular-shaped bioreactors so that the reaction solution passes through only a rather narrow thickness of matrix from the point where the reactants enter the matrix to the point where the products exit the matrix. As a result, the reaction products remain within the matrix for only a relatively short time. Thus, the residence time is relatively constant, regardless of where along the length of the tubular matrix the reaction takes place, thereby minimizing degradation and unwanted side-reactions and thereby also providing remarkable control over the reaction parameters, rates and conditions.

The use of a ceramic matrix member is extremely advantageous because ceramic is thermally, chemically, and mechanically stable. Further, by "backflushing" the system with a suitable solvent, the matrix member may be readily cleaned. The ceramic matrix member may then be sterilized for reuse.

It is, therefore, a primary object of the present invention to provide methods and apparatus for conducting chemical and biological reactions in a manner that allows for improved control over reaction parameters, particularly at the location where the reaction is occurring.

It is another object of the present invention to provide methods and apparatus for conducting chemical and biological reactions in a manner that will minimize degradation and unwanted side-reactions of products which are formed.

It is a further important object of the present invention to provide methods and apparatus for maximizing the yield of reaction products in chemical and biological reactions.

It is still a further object of the present invention to provide methods and apparatus for separating products of chemical and biological reactions from the reactants.

Yet a further object of the present invention is to provide apparatus for conducting chemical and biological reactions that can be readily cleaned and sterilized between uses.

These and other objects and features of the present invention will become more fully apparent from the following description and appended claims taken in conjunction with the accompanying drawings.

BRIEF DESCRIPTION OF THE DRAWINGS

In the accompanying drawings, which represent the best mode presently contemplated for carrying out the present invention.

DETAILED DESCRIPTION OF THE PREFERRED EMBODIMENTS

Figure 1:
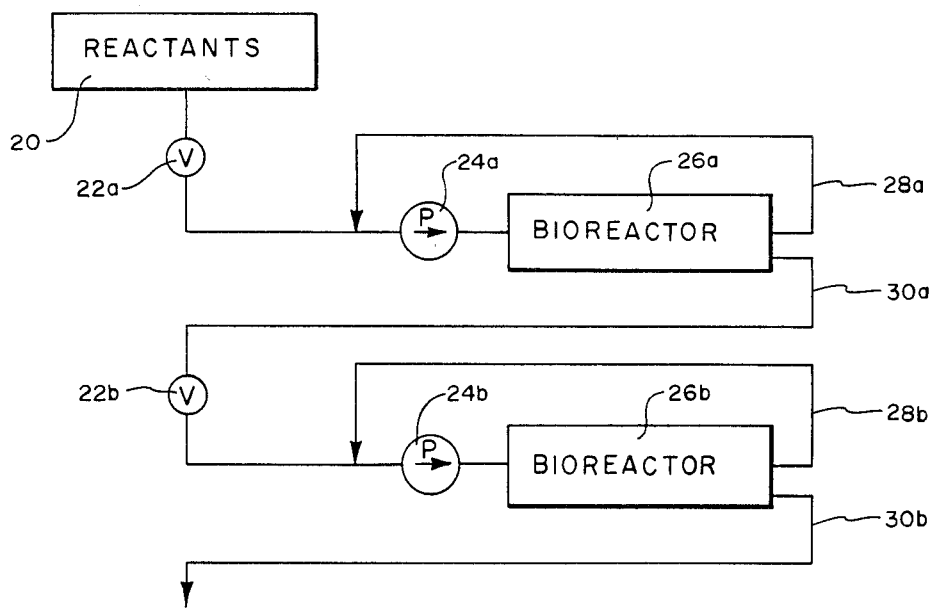
FIG. 1 is a schematic diagram indicating how a pair of bioreactors fabricated in accordance with the present invention may be placed into a system for conducting biochemical reactions.

The present invention can best be understood by reference to the drawings, wherein like parts are designated with like numerals throughout. FIG. 1 is a schematic diagram of a typical reaction system incorporating a bioreactor constructed in accordance with the present invention. While much of the following detailed description is presented in terms of chemical reactions involving biological materials, it will be appreciated that the present invention is equally applicable to other types of chemical reactors involving a variety of different reactants. Thus, it will be appreciated that the use of terms such as "bioreactor" are not intended to restrict the scope of the invention to use only with biological materials and that such terms are used generically.

With specific reference to FIG. 1, it is seen that a solution of reactants 20 is introduced through a valve 22a and a pump 24a into a bioreactor 26a. Unused reactants are removed from bioreactor 26a through line 28a, and thereafter returned to the bioreactor through pump 24a. Reaction products, and unused reactants and various by-products, to the extent that they exist, are removed from the bioreactor through line 30a.

In some applications of the present invention, the solution drawn off from bioreactor 26a through line 28a will be suitable for immediate use. In other applications, however, it may be either necessary or desirable to pass this solution through a second bioreactor 26b, as shown in FIG. 1. In these cases, a valve 22b and pump 24b are advantageously provided to perform functions similar to valve 22a and pump 24a in the first-stage bioreactor 26a.

One situation for which a second-stage bioreactor may be used is where a first reaction takes place in the first bioreactor, and a second reaction utilizing the product of the first bioreactor is conducted in a second bioreactor. It will be appreciated that the solution leaving the second bioreactor through line 30b may be fed into yet additional bioreactor stages as may be necessary or desirable for a given application of the present invention.

It may also be desirable in some instances to use multiple stages of bioreactors in circumstances where unused reactants accompany the reaction products exiting the first stage bioreactor, thereby increasing the concentration of products in the solution finally collected from the system.

Figure 2:
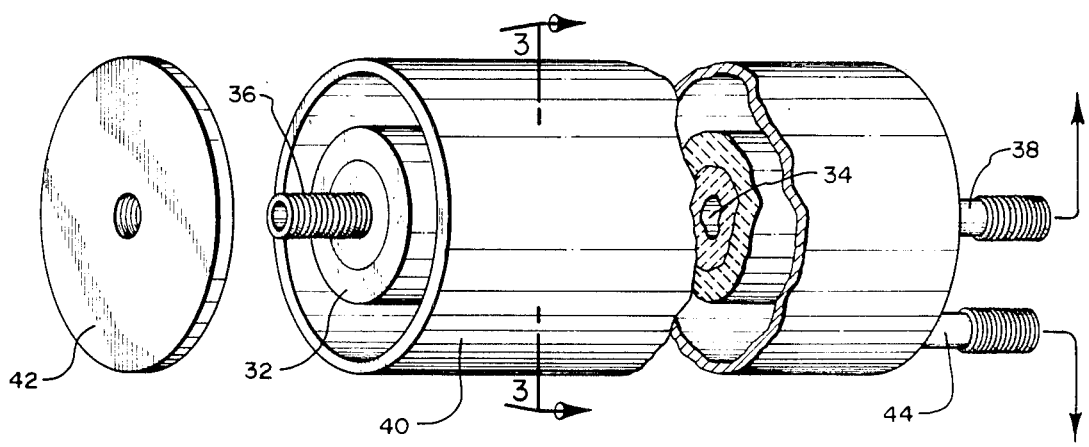
FIG. 2 is a partially exploded perspective view of a presently preferred embodiment of a bioreactor constructed in accordance with the present invention, with a portion thereof shown cut away for convenience of illustration.

One specific embodiment of a bioreactor constructed in accordance with the present invention is illustrated in FIG. 2. In FIG. 2, it will be seen that the bioreactor includes a bioreactor matrix member 32 having a bore 34 therethrough into which is secured a connector 36 that is adapted for securement to a reaction solution supply line (not shown). A second connector 38 is secured to the opposite end of bore 34, and may be used to collect unused reaction solution for feeding to a discharge line (not shown) for recirculation in the manner shown with respect to line 28a of FIG. 1.

Matrix member 32 is securely fixed within an enclosed liquid tight vessel 40, that may advantageously be provided with a removable end cap 42. As set forth in greater detail hereinbelow, a drain connector 44 is provided to permit removal of solution collected within vessel 40.

Matrix member 32 is preferably constructed from a ceramic material in a manner that causes the material to be microporous. Sintered ceramic materials are preferred for use in fabricating the matrix member because they provide high mechanical stability such that they maintain their integrity during handling and under the pressures that may be involved in use, as well as other operations such as cleaning and sterilization. The manner of making porous ceramic devices, which as discussed below may comprise multiple layers of ceramic having different porosities, is disclosed in copending patent application Ser. No. 06/550,746 filed Nov. 9, 1983, for "Apparatus and Methods For Therapeutic Aphoresis," also assigned to the assignee of the present application, said copending application being incorporated herein by reference in its entirety. Information relating to formation of a porous course-grained ceramic support holding a thinner filtering layer of fine-grained fritted material is set forth in French Pat. No. 2,502,508.

Equally important, sintered ceramic materials are preferable for use in the matrix member because such materials are inert to most chemical reactants and biological materials, and are also corrosion resistant. Additionally, the pores of a matrix member constructed from sintered ceramic material as set forth herein and in copending application Ser. No. 06/550,746, tend to be asymmetric in shape. The use of asymmetric pores tends to avoid blockages within the pores when chemical reactants or biological materials are fixed therein. This feature greatly facilitates pressure-driven fluid management, as will be better appreciated from the subsequent discussion.

Alumina and alumina silicates are the preferred materials for use in constructing porous ceramic matrix member 32 because of the chemical stability of these materials. However, a wide variety of other ceramic materials may be utilized in construction of the microporous matrix member. Thus, it is anticipated that suitable matrix members can, depending upon the particular chemical or biological reactions involved, be constructed from one of the various oxides in crystalline or glassy form of aluminum, silicon, zirconium, titanium, chromium, and magnesium; carbides of silicon, or the like; nitrides (such as silicon nitride); or various minerals such as cordierite, mullite, and the like. Mixtures or combinations of one or more of the foregoing may also be used for certain applications.

As will be better appreciated from the subsequent discussion, the average pore size should generally be within the range of from about 0.01 microns to about 50 microns, and preferably in the range of from about 0.05 microns to about 10 microns. The optimum size will depend upon the particular chemical or biological materials and reactants to be used in the reaction. Utilization of a matrix member having a pore size in the range set forth above will result in a microporous ceramic membrane exceptionally well-suited for use as a bioreactor component in many biological reactions.

Initially, the reactor matrix member is preferably prepared for use by treatment with an appropriate fixing agent; various silanes and olefins are known to be capable of fixing many biological materials used in common bioreactions. This initial treatment will leave a very thin layer of the fixing agent within the pores of the matrix.

After the pores of the matrix have been pretreated so as to contain a thin layer of the fixing agent, the appropriate chemical or biological materials (for example, in the case of a typical bioreactor, whole or lysed cells, cell extracts, purified enzymes, or the like might be used) are added to the system so that the chemical or biological materials become fixed within the various pores of the matrix. Methods for fixing enzyme and chemical catalyst materials into a ceramic matrix are set forth in U.S. Pat. Nos. 4,384,043 and 4,239,854, which patents are hereby incorporated by reference.

In its simplest form, the reactor matrix may be constructed so as to have a substantially uniform pore size throughout, therefore being isotropic along the fluid flow path, with the reactor matrix member serving as a high surface area support for the chemical or biological material. However, as discussed in greater detail below, it will be very desirable for most applications to provide multiple layers of ceramic material, each layer having different pore sizes. Use of multiple layers of ceramic having different porosities results in an anisotropic matrix member; the provision of an anisotropic matrix member is a very important feature of the present invention. The thickness of each layer may also be varied from that of other layers, depending upon the specific reaction system.

Figure 3:
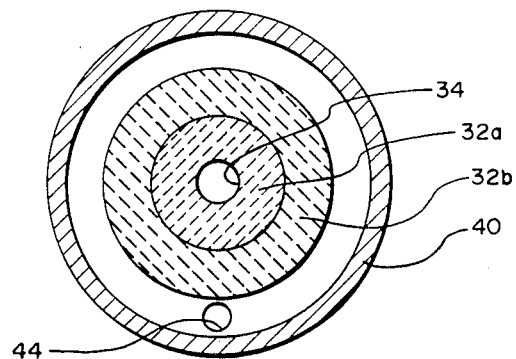
FIG. 3 is a transverse cross-sectional view taken along the line 3—3 of the embodiment of the reactor illustrated in FIG. 2.

With specific reference to FIG. 3, a reactor matrix member comprised of two layers 32a and 32b of microporous ceramic material is illustrated. In the embodiment of the ceramic matrix member of FIG. 3, layer 32a is advantageously adapted to receive the chemical or biological materials within its pores, but layer 32b has a smaller pore size such that the particular chemical or biological materials being used will not pass therethrough. This configuration of the ceramic matrix insures that the chemical or biological materials are maintained within layer 32a.

Depending upon the reaction involved, it will at times be practical to select an appropriate pore size for layer 32b such that the reaction products will pass through the pores of layer 32b, but the reactants will not pass through these pores. This configuration thus serves to separate the products from the reactants and to potentiate the reaction by retaining and concentrating the reactants within reaction layer 32a.

When utilizing a tubular matrix member such as is illustrated in connection with the embodiment of the reactor illustrated in FIG. 2, reaction solution is advantageously introduced into bore 23 under a pressure sufficient to drive a controlled amount of solution into porous ceramic matrix 32. Controlling the rate of flow of solution through the reactor matrix member is one manner of controlling the reaction rate and the efficiency of the reaction. Increasing the reaction solution inlet pressure will increase the flow rate of reaction solution through the matrix; conversely, reducing the pressure at the reaction solution inlet will reduce the flow therethrough. Adjusting the thickness of the ceramic matrix member is also an important determinant of flow rate; at a given solution inlet pressure, the flow rate is inversely proportional to the thickness of the matrix member. Thus, when providing one or more layers in the ceramic matrix member having very small pore sizes, it will generally be advantageous to minimize the thickness of these layers. In accordance with the present invention, very thin layers of ceramic material may be utilized because they will be structurally supported by an adjacent porous layer of the matrix member.

The number of pores in the matrix member, which controls the surface area available for fixation of the chemical or biological materials, also affects the reaction rate. Similarly, the diameter of the pores in the matrix member affects the reaction rate; thus a small diameter tends to restrict the flow of reaction solution therethrough. Additionally, the size of the matrix pores directly affects the ratio of the amount of the reaction solution to the amount of the chemical or biological material contained within the reactor matrix member; this ratio is another determinant of reaction rate. From the foregoing, it will be readily appreciated that great control over the reaction rate can be achieved by controlling the size, diameter, and number of pores in the ceramic matrix member.

As indicated above, the reaction solution is pumped into bore 34 of the reactor matrix member under sufficient pressure to cause suitable flow of reaction solution into the matrix for reaction with the biological material fixed therein. Products, and in some cases unused reactants, will pass through matrix layers 32a and 32b, and finally emerge from the outer surface of the bioreactor matrix member; here, the products (and any unused reactants) will collect within vessel 40.

As mentioned above, vessel 40 is preferably enclosed, although it will be appreciated that this is not necessary; all that is required is that the vessel serve to collect the solution emerging from the reactor matrix member. The solution collected within vessel 40 is withdrawn through drain 44 for feeding into subsequent reactor stages or for some other intended use.

As fluid passes through bore 34, because of the pressure differential between the fluid in the bore and the pressure within housing 40, a portion of the fluid flows into and through the ceramic matrix member. This type of fluid flow described above is generally termed "cross-flow". A cross-flow system is very advantageous for some reaction systems. For instance, use of a cross-flow system such as illustrated in FIGS. 2 and 3 tend to result in substantially equal amounts of fluid flow into the ceramic matrix member at virtually any point on the surface of bore 34. Additionally, fluid flow across the surface of bore 34 assists in dislodging any particles that are too large to enter the pores of the ceramic matrix member. Also, in systems wherein the fluid introduced into bore 34 contains components that are incapable of passing into the matrix member, the use of a cross-flow system prevents such components from collecting and concentrating within the bore.

However, the present invention is also suitable for use in situations where "through-flow" of fluid is desired. For instance, connector 38 could be capped so as to prevent any solution pumped into bore 34 from leaving the reactor other than by passing through the matrix member. The difference between a cross-flow and through-flow system is that in a through-flow system the only outlet for fluid introduced into the reactor is from the permeate collection region within housing 40.

In addition to the remarkable control over reaction parameters that are possible in connection with the novel ceramic matrix member, the ceramic matrix member is also remarkably easy to cleanse for reuse. Thus, the matrix member may be easily cleansed by introducing a suitable solvent, under pressure, so as to induce solvent flow in a direction opposite that of fluid flow under normal conditions of use. This "backflushing" of the matrix member serves to dislodge particulate materials from the various pores of the matrix member and to strip the pores of the fixing agent as well as the chemical or biological material fixed within the pores of the matrix member. Due to the thermal stability of ceramic materials, the matrix member may then be sterilized under conditions of heat (such as in an autoclave) in preparation for reuse.

Figure 4:
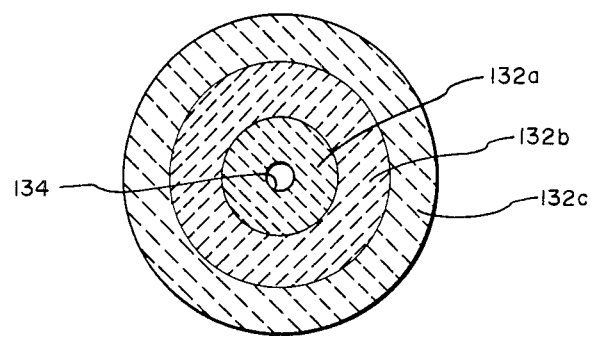
FIG. 4 illustrates a transverse cross-sectional view of another embodiment of a porous ceramic reactor matrix member constructed in accordance with the present invention.

A second embodiment of a porous ceramic reactor matrix member within the scope of the present invention is illustrated in FIG. 4. This embodiment of the matrix member comprises three layers 132a, 132b, and 132c of successively decreasing pore sizes, with a bore 134 being provided through innermost layer 132a. The embodiment of FIG. 4 is useful in situations where the desired reaction product is smaller in size than the reactants (or undesirable by-products). Appropriate selection of the pore size in layer 132c will result in a porous layer permitting only the reaction product to pass through matrix layer 132c for eventual collection in the bioreactor vessel (not shown), with other solution components being retained in layer 132b. (Again, it is to be understood that although FIG. 4 is drawn in a manner that makes it appear that layers 132a, 132b, and 132c each have identical thicknesses, in actual practice these layers may greatly differ in thickness.)

Figure 5:
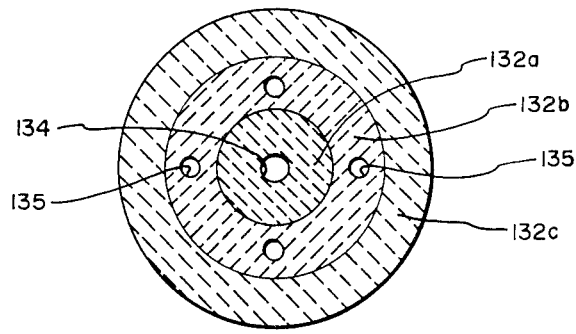
FIG. 5 illustrates a transverse cross-sectional view of a third embodiment of a porous ceramic reactor matrix member constructed in accordance with the present invention.

A useful modification to the bioreactor matrix of FIG. 4 is illustrated in FIG. 5, which depicts the addition of lumens 135 within matrix layer 132b. It is to be understood that, while four lumens 135 are illustrated in FIG. 5, either a greater number or a fewer number of such lumens may be provided. These lumens can be used to withdraw solution from intermediate layer 132b of the embodiment illustrated in FIG. 5 in addition to being able to collect solution emerging from the outermost layer 132c. Alternatively, in certain applications, it may be desirable to introduce the reactants into the system through lumens 135. Where desired, the lumens may themselves be lined with thin layers (not shown) of microporous ceramic material in order to selectively restrict flow of fluid components between the lumens and layer 132b of the matrix member.

The flexibility of the present invention will be appreciated from the fact that, after fixing the chemical or biological material in innermost matrix layer 132a, it would be possible to introduce a chemical or biological material having a lower molecular weight into lumens 135 for fixing within porous matrix layer 132b. This is useful where a secondary reaction is desired, with the product of the reaction of matrix layer 132a being immediately fed to layer 132b for additional reaction. This is particularly advantageous where the product of the first reaction is unstable or likely to undergo additional unwanted side reactions. The applicability of this embodiment to chemical reactors requiring the generation and use of unstable chemical intermediates will be readily appreciated.

Figure 6:
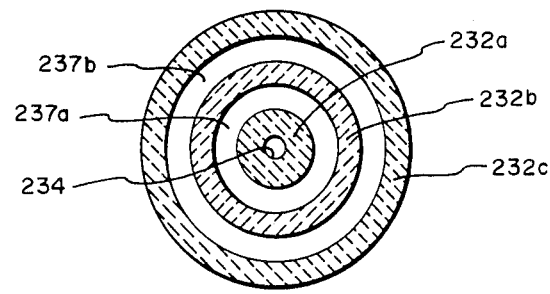
FIG. 6 illustrates a transverse cross-sectional view of a fourth embodiment of a porous ceramic reactor matrix member constructed in accordance with the present invention.

FIG. 6 illustrates yet another embodiment of a three-layer reactor matrix member constructed in accordance with the present invention. In FIG. 6, it may be seen that matrix layers 232a, 232b, and 232c are spaced sufficiently apart to allow solution to collect therebetween. Pressure from reaction solution introduced into bore 234 will cause spaces 237a and 237b to fill with solution, and then to pass through the respective next outer layer, 232b and 232c. This construction allows for ease of placement (and of replacement) of individual porous membranes.

One advantage of this embodiment is that it permits replacement of clogged matrix layers or of layers containing expended biological material, without requiring replacement of the entire matrix member. This embodiment also provides for fixing the chemical or biological material to the appropriate matrix layer before installation of the matrix layer into the reactor.

Another advantage of this embodiment is that it provides a space for removing portions of the solution contained within spaces 237a and 237b; this can be particularly advantageous when it is necessary to monitor the extent of a reaction occurring in the preceding matrix layer. In addition, as with lumen 135 of FIG. 5, solution containing additional reactants could be introduced into the spaces 237a or 237b for entry into the system.

It will be appreciated from the foregoing discussion that many other embodiments and modifications of the reactor matrix member are possible, and a suitable matrix member may be designed for each particular reaction system. Although each of the illustrated embodiments contemplate application of reaction solution to the bore of a tubular matrix member, and collection from the exterior thereof, it is to be appreciated that reaction solution could alternatively be introduced into the bioreactor vessel through drain 44 and collected from the bore of the matrix member, or from lumens within one of the matrix layers. It should also be understood that whereas the illustrated embodiments all depict tubular matrix members, it would be possible to utilize other shapes, such as simple flat microporous ceramic shapes.

It is presently preferred that a porous ceramic reactor matrix constructed in accordance with the present invention will have an overall diameter in the range from about 2 millimeters to about 20 millimeters, with the presently most preferred range being from about 3 millimeters to about 10 millimeters. A typical porous ceramic matrix layer will preferably have a thickness in the range from about 5 microns to about 10 millimeters, with the most preferred range being from about 10 microns to about 5 millimeters. When utilizing a very thin porous ceramic matrix layer, an adjacent layer of relatively high porosity and sufficient thickness to insure structural integrity should generally be provided to serve as a support layer for the thin layer. Use of a highly porous support layer will have little effect on the flow rate of the system, yet will insure that even very thin microporous layers of ceramic material neither deform nor degrade as a result of high system pressures.

It will be appreciated that the porous ceramic reactor matrix member can be of any convenient length. Since the reaction solution travels radially through the matrix, the length of the matrix has little or no effect on the reaction system other than the effect on the volume of reaction solution that will be processed. In order to utilize rather short reactor matrix members, yet have a relatively high volume throughput, it may be desirable to provide a multiplicity of relatively short matrix members secured within a single vessel, such as is illustrated in FIG. 7.

Figure 7:
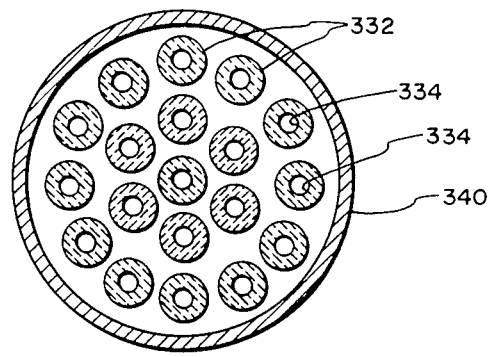
FIG. 7 illustrates a transverse cross-sectional view of a fifth embodiment of a reactor that utilizes a plurality of porous ceramic matrix members installed in parallel to the reaction solution.

In such a configuration, bores 334 of the various matrix members 332 of FIG. 7 are preferably interconnected to the reaction solution supply and discharge lines (not shown) through suitable headers (also not shown) provided at each end of collection vessel 340. A single drain (not shown) in vessel 340 could be used to collect solution emitted from the various reactor matrix members.

From the foregoing, it will be appreciated that the present invention provides methods and apparatus for conducting biological reactions in a manner that allows unprecedented control over reaction conditions, parameters, and rates. Selection of number, size, diameter, and distribution can be used to potentiate a particular reaction system. Other design parameters include a determination of the number and thickness of porous membrane layers to provide, whether or not to provide lumens within some matrix layers, and whether or not to space some porous layers apart from one another.

All of these design parameters can be selected either empirically and/or experimentally with respect to a particular reaction system. Appropriate manipulation of these various parameters will permit control over bioreactions never before possible in a commercial environment.

The present invention can also be used to prevent or minimize unwanted degradation of reaction products or side reactions in those instances where such side reactions are likely to occur. Most simply, use of appropriate porous layers can isolate reaction products from the reactants so that no additional unwanted reactions are possible. Also, the actual distance to be traversed by reaction solution is relatively narrow; the solution need travel only the relatively short distance from the bore to the outside surface of the tubular matrix member. Further, the reactor of the present invention can be designed to be a continuous system, where products are quickly removed from the reactor.

Yet another important advantage of the present invention is the ability of anisotropic microporous membranes forming a bioreactor matrix member to cause partial or even substantial separation of product from reactants and by-products. This is useful in many cases because the product solution can be used immediately without the need for intervening purification steps.

Yet a further advantage of the present invention is due to the marvelous thermal, chemical, and mechanical stability of a matrix member constructed from a ceramic material; this avoids degradation of the matrix member, avoids unwanted side reactions between the reactants and the matrix material, and the like. Since the ceramic matrix member may be readily cleaned and sterilized, a ceramic matrix member constructed in accordance with the present invention may also be reused many times.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A reactor comprising:
   (a) an integral, coherent, fluid-permeable ceramic matrix having a plurality of porous layers, each of said layers having pores of a size within the range of about 0.01 microns to about 50 microns;
   (b) a reagent material fixed within said ceramic matrix;
   (c) means for introducing a first mobile reactant dispersed in a fluid into the pores of the matrix, thereby bringing the mobile first reactant into contact with the fixed reagent so that the mobile first reactant may react chemically with the fixed reagent; and
   (d) a vessel containing said matrix and collecting a product of reaction between said first mobile reactant and said fixed reagent.

2. A reactor according to claim 1, wherein each of the plurality of porous layers of the ceramic matrix has an average pore size different from the average pore size of an adjacent layer.

3. A reactor according to claim 2 wherein said ceramic matrix defines an input space and an output space within said vessel such that the only path by which fluid can pass between said input space and said output space is through each of the distinct porous layers of said ceramic matrix.

4. A bioreactor comprising:
   (a) a porous ceramic matrix generally tubular in shape and comprising a plurality of generally concentric layers of progressively decreasing porosity such that the innermost layer of the ceramic matrix has the largest pore size and the pores have a size within the range of about 0.01 microns to about 50 microns, said ceramic matrix having an axial bore through the center;

(b) means for introducing into said axial bore a solution containing a first and a second reactant, at least said first reactant being unable to pass through at least one layer of said ceramic matrix, said first and second reactants being capable of reaction to form a product capable of passing through all layers of said ceramic matrix;

(c) means for placing the reactant-containing solution under sufficient pressure in the axial bore to cause at least a portion of the reactant-containing solution to pass through at least the innermost layer of the ceramic matrix; and (d) a vessel containing said matrix and collecting, separately from the reactant solution introduced into the axial bore, any solution which passes through all layers of the ceramic matrix.

5. A method for reacting a biological reagent with at least one suitable reactant, comprising the steps of:

(a) providing a reactor comprising: (i) an integral, coherent, fluid-permeable ceramic matrix having a plurality of porous layers, each of said layers having pores of a size within the range of about 0.01 microns to about 50 microns; (ii) said biological reagent is fixed within said ceramic matrix; (iii) means for introducing said at least one reactant dispersed in a fluid into the pores of the matrix, thereby bringing the at least one reactant into contact with the fixed reagent so that the at least one reactant may react chemically with the fixed reagent; and (iv) means for collecting a product of reaction between said at least one reactant and said fixed reagent;

(b) introducing on one side of said ceramic matrix a solution containing the at least one reactant into the pores of the ceramic matrix within which the biological reagent is fixed, so as to allow the reaction of the at least one reactant with the biological reagent;

(c) passing solution containing product of the reaction of step (b) through all layers of the ceramic matrix between the part of the ceramic matrix in which the reaction according to step (b) occurs and the side of said ceramic matrix opposite the side of introduction of solution thereinto according to step (b); and (d) collecting solution passing through the ceramic matrix in step (c) separately from the solution of reactants introduced in step (b).

6. A method for reacting a first chemical material with a second chemical material, comprising the steps of:

(a) providing a reactor comprising: (i) an integral, coherent, fluid-permeable ceramic matrix having a plurality of porous layers, each of said layers having pores of a size within the range of about 0.01 microns to about 50 microns; (ii) said first chemical material is fixed within said ceramic matrix; (iii) means for introducing said second chemical material dispersed in a fluid into the pores of the matrix, thereby bringing the second chemical material into contact with the first chemical material so that the second chemical material may react chemically with the fixed first chemical material; and (iv) means for collecting a product of reaction between said first and said second chemical materials;

(b) introducing on one side at said ceramic matrix a solution containing the second chemical material into the pores of the ceramic matrix within which the first chemical material is fixed, so as to allow the reaction of the second chemical material with the first chemical material;

(c) passing solution containing product of the reaction of step (b) through all layers of the ceramic matrix between the part of the ceramic matrix in which reaction according to step (b) occurs and the side of said ceramic matrix opposite the side of introduction of solution thereinto according to step (b); and (d) collection solution passing through the ceramic matrix in step (c) separately from the solution introduced in step (b).

7. A method according to claim 6, wherein each layer of said plurality of layers of said ceramic matrix has a pore size different from the pore size of an adjacent layer.

8. A method according to claim 7, wherein said collecting means comprises a housing which together with said ceramic matrix defines an input space and an output space within said housing and a flow path which only allows fluid to pass between said input space and said output space through each of the distinct porous layers of said ceramic matrix, and the pore size of the layer of said ceramic matrix having the smallest pore size is large enough to permit a product of reaction between said first and said second chemical materials to pass therethrough but too small to permit either the first or the second chemical materials to pass therethrough.

9. A method for reacting a first and a second reactant capable of chemical reaction to produce a product capable of passing through a layer of permeable material having pores of sufficiently small size to prevent said first reactant from passing therethrough, comprising the step of:

(a) providing a bioreactor comprising: (i) an integral, coherent, fluid-permeable ceramic matrix generally tubular in shape and having a plurality of generally concentric layers of progressively decreasing controlled pore size such that the innermost layer of the ceramic matrix has the largest pore size, each of said layers having pores of a size within the range of about 0.01 microns to about 50 microns and the layer with the smallest pore size being impermeable to said first reactant, said ceramic matrix having an axial bore through its center; (ii) means for introducing into said axial bore a solution containing said first and said second reactants; (iii) means for placing the reactants containing solution within said axial bore to sufficient pressure to cause at least a portion of said solution containing a product of reaction between said first and said second reactants to pass through all layers of said ceramic matrix; and (iv) means for collecting, separately from the reactant solution introduced into the axial bore, any solution which passes through all layers of the ceramic matrix;

(b) introducing a solution of said first and second reactants into the axial bore of said matrix;

(c) applying sufficient pressure to the reactant solution within said axial bore to cause at least some solution containing a product of the reaction between the first and second reactants to pass through all layers of said ceramic matrix between the axial bore and an outer side of said ceramic matrix; and (d) collecting solution passing through the ceramic matrix in step (c) separately from the solution introduced in step (b).

* * * * *